United States Patent [19]

Orr et al.

[11] 4,066,756

[45] Jan. 3, 1978

[54] THERAPEUTIC COMPOSITIONS OF 1,3-BIS(2-CARBOXYCHROMON-5-YLOXYL)-PROPAN-2-OL AND ASPIRIN OR INDOMETHACIN

[75] Inventors: Thomas Samuel Campbell Orr, Melton Mowbray; David Edward Hall, Burton-on-the-Wolds; John Mann, Long Whatton, all of England

[73] Assignee: Fisons Limited, London, England

[21] Appl. No.: 742,750

[22] Filed: Nov. 18, 1976

[30] Foreign Application Priority Data

Nov. 28, 1975 United Kingdom ............... 48935/75

[51] Int. Cl.² .................... A61K 31/35; A61K 31/40; A61K 31/625

[52] U.S. Cl. .................................... 424/232; 424/274; 424/283

[58] Field of Search ................ 424/232, 278, 283, 274

[56] References Cited

U.S. PATENT DOCUMENTS 3,419,578  12/1968  Fitzmainio ........................... 424/278

*Primary Examiner*—Stanley J. Freidman
*Attorney, Agent, or Firm*—Merriam, Marshall & Bicknell

[57] ABSTRACT

There is described a pharmaceutical mixture comprising 1,3-bis(2-carboxychromon-5-yloxy)propan-2-ol, or a pharmaceutically acceptable salt thereof, and aspirin or indomethacin. The mixture causes less gastrointestinal adverse effects than aspirin or indomethacin on their own.

14 Claims, No Drawings

THERAPEUTIC COMPOSITIONS OF 1,3-BIS(2-CARBOXYCHROMON-5-YLOXYL)PROPAN-2-OL AND ASPIRIN OR INDOMETHACIN

This invention relates to a mixture and a method for its preparation.

Aspirin, indomethacin and a number of other anti-inflammatory agents are widely used in the treatment of inflammatory conditions, but suffer from the disadvantage that they can cause gastro-intestinal irritation, pain, nausea, indigestion and in particular gastro-intestinal micro bleeding. We have now surprisingly found that the gastro-intestinal side effects of the anti-inflammatory agents indomethacin and aspirin can be inhibited by the application of di-sodium cromoglycate in combination with the anti-inflammatory.

According to our invention therefore we provide a pharmaceutical composition comprising 1,3-bis(2-carboxychromon-5-yloxy)propan-2-ol, or a pharmaceutically acceptable salt thereof, (herein referred to collectively as 'active ingredient') in combination with aspirin or indomethacin.

We prefer to use the di-sodium salt of 1,3-bis(2-carboxychromon-5-yloxy)propan-2-ol, which is commonly known as disodium cromoglycate (DSCG) or cromolyn sodium.

When aspirin is used a suitable ratio of the compounds in the combination is from about 6,000 to 0.12 parts, preferably from 600 to 0.3 parts, and more preferably 600 to 1.2 parts by weight of aspirin to each part by weight of active ingredient. When indomethacin is used a suitable ratio of the compounds in the combination is from 0.02 to 1,000, preferably from 0.05 to 100, and more preferably from 0.3 to 100 parts by weight of indomethacin to each part by weight of active ingredient.

When aspirin is used a suitable daily dosage for most anti-inflammatory purposes is in the range 3 to 80 mg per kg, and preferably 3 to 40 mg per kg, of the subject to be treated's body weight. Thus for an adult human the normal dosage is in the range of from about 180 mg to 4.8g per day, and preferably from 180 mg to 2.4g per day, preferably given in divided doses 3 to 8, and preferably 3 to 4 times per day. When indomethacin is used a suitable daily dosage for most anti-inflammatory purposes is in the range 0.33 to 8.33 mg, and preferably from 0.83 to 8.33 mg, per kg of the subject to be treated's body weight. Thus for an adult human the normal dosage is in the range of from about 20 to 500 mg per day, preferably given in divided doses 2 to 5, and preferably 2 to 3 times per day. In the case of both aspirin and indomethacin each dose may comprise one or more unit doses, e.g. tablets or capsules.

For human use therefore we provide compositions in unit dosage form comprising from 60 to 600 mg of aspirin and from 0.1 to 500 mg, preferably from 1 to 200 mg, and more preferably from 1 to 50 mg of active ingredient. Also for human use we provide compositions in unit dosage form comprising from 10 to 100 mg, and preferably from 25 to 100 mg, of indomethacin and from 0.1 to 500 mg, preferably from 1 to 200 mg, and more preferably from 1 to 50 mg, of active ingredient in unit dosage form. We particularly prefer compositions in unit dosage form comprising up to 100 mg of active ingredient as higher unit doses of active ingredient may tend to cause an increase in gastrointestinal irritation.

According to our invention we also provide a method for the treatment of an inflammatory and/or painfull condition, e.g. arthritis such as rheumatoid arthritis, rheumatism and other disorders, e.g. inflammatory disorders or platelet aggregation, normally treated with aspirin or indomethacin, which comprises administration of a composition according to the invention to an individual mammal, e.g. human, suffering from such a condition. The administration is preferably per os, and is most preferably administration by mouth (oesphagaeal administration).

According to the invention we also provide a method for the treatment of an inflammatory and/or painfull condition, e.g. arthritis such as rheumatoid arthritis, rheumatism, and other disorders, e.g. inflammatory disorders or platelet aggregation, normally treated with aspirin or indomethacin, which comprises sequential or simultaneous administration of active ingredient and indomethacin or aspirin to an individual mammal, e.g. human, suffering from such a condition or disorder.

The active ingredient is preferably administered in such a way that it is available in the gastrointestinal tract before the aspirin or the indomethacin, e.g. the active ingredient may be administered before the aspirin or indomethacin. Alternatively the active ingredient may be administered together with or after the aspirin or indomethacin, but in such circumstances the aspirin or indomethacin are preferably used in delayed or sustained release form.

When sequential or simultaneous administration of active ingredient and aspirin or indomethacin is used the ratios and dosages of the active ingredient and aspirin or indomethacin are as described above with respect to the mixtures.

The invention therefore also provides a pharmaceutical package comprising at least one unit dose of active ingredient and at least one unit dose of indomethacin or aspirin. The unit doses are preferably arranged in the package in a particular order together with written or printed indications or directions, the indications or directions and the manner of packing being such as to provide guidance in relation to and to facilitate the taking of a unit dose of active ingredient and a unit dose of aspirin or indomethacin in a particular order, e.g. a unit dose of the former before a unit dose of the latter. The package is preferably a sealed package and may comprise a tube, box or chart in or on which the unit doses are packed. The unit doses are preferably suitable for oesphagaeal administration and preferably contain the doses of active ingredient and indomethacin or aspirin in the ratios set out above for the combinations.

The suppression of the side effects of the aspirin or the indomethacin may be further enhanced by the post — or preferably pre-dosing of the subject with additional active ingredient.

In order to produce suitable compositions the active ingredient and the aspirin or indomethacin, either separately or as a mixture thereof, are worked up with organic or inorganic pharmaceutically acceptable adjuvants or excipients. Examples of such adjuvants are:

For tablets and dragees: Binders, for example, cellulosic materials, e.g. microcrystalline cellulose and methyl cellulose; disintegrating agents, for example starches, e.g. maize starch; stabilisers, e.g. against hydrolysis of the active ingredients; flavouring agents, for example sugars such as lactose; fillers; stearates and inorganic diluents, e.g. talc.

For syrups, suspensions or dispersions: A liquid vehicle in which the active ingredients may be dissolved or suspended, e.g. water; and suspending agents, e.g. cellulose derivatives, gums etc.

For hard or soft capsules: Diluents, e.g. lactose; glidants, e.g. stearates; inorganic materials, e.g. silica or talc; stabilizers and dispersing agents.

For suppositories: Natural or hardened oils, waxes etc. A large number of proprietary emulsifying bases are available and are suitable for use in suppositories. These include 'Witepsol' bases, consisting of hydrogenated triglycerides of lauric acid with added monoglycerides; and 'Massupol' bases, which consist of glyceryl esters of lauric acid with a very small amount of glyceryl monostearate.

For enemas: Water, sodium chloride, buffers etc.

We prefer compositions which are designed to be administered by mouth (oesophagaeally).

The composition may also contain further adjuvants, for example a composition for use in tablets may contain lubricants and glidants to assist in tabletting, e.g. magnesium stearate, or wetting agents to assist in granulation, e.g. dioctyl sodium sulphosuccinate. The compositon may also if desired contain a pharmaceutically acceptable dye or colourant, and may, if desired, be coated using conventional film or sugar coating techniques.

If desired the composition, or one or more components thereof, may be formulated in sustained release form, e.g. by coating some or all of the drug particles themselves or granules thereof made with, for example, sucrose and of a size up to 2 mm in diameter with a layer of, e.g. beeswax, Carnuba wax, stearic or palmitic acids, cetyl alcohol or similar substances which could be expected to be slowly dissolved or digested or to act as semi-permeable membranes through which the active ingredients can diffuse when the preparations are ingested. The composition may contain drug particles or granules which are uncoated in admixture with particles or granules having one or more coats of the coating medium, and may be in the form of a capsule containing the particles or granules or alternatively a tablet, for which other adjuvants may be required, such as glidants or lubricants. The mixture may be administered as an enteric coated composition to make the active ingredients available at the appropriate part of the gastro-intestinal tract. This may be achieved by coating the tablet with a continuous film of material which is resistant and impermeable to gastric secretions, but which is susceptible to intestinal secretions. Typical film materials are shellac and its derivatives and cellulose acetate phthalate.

We prefer compositions which are adapted to release some or all of the active ingredient first and to release the aspirin or indomethacin later. Thus a solid composition may comprise a core of aspirin or indomethacin surrounded in part or in whole by an outer layer containing the active ingredient. The core may, if desired or necessary, be coated with a material which is relatively slowly dissolved or degraded by the gastric juices, e.g. shellac, beeswax, Carnuba wax, stearic or palmitic acids, or cetyl alcohol or the like and this coating may in turn be coated with a material containing the active ingredient which is relatively quickly dissolved or degraded by the gastric juices, e.g. sugar or a cellulose ether such as hydroxypropylmethylcellulose. Alternatively the composition may comprise discrete particles of the active ingredient, which may be coated or uncoated, but which are adapted to dissolve or disperse quickly in the gastrointestinal tract, in admixture with discrete particles of aspirin or indomethacin which are preferably coated or treated so that they dissolve or disperse the aspirin or indomethacin slowly in the gastrointestinal tract. We prefer the composition to be such that the aspirin or indomethacin begin to be available in the gastrointestinal tract from about 5 to 15 minutes after the active ingredient commences to be available in the gastrointestinal tract.

The active ingredient and the indomethacin or aspirin may, if desired, be used in a specific form, e.g. having a mass medium diameter of less than 10 microns.

The active ingredient and the indomethacin or aspirin may also be formulated as an aqueous, e.g. a water chloroform (400:1), solution containing from 0.001 to 10.0% by weight of the active ingredient plus the indomethacin or aspirin.

We prefer compositions containing aspirin.

The invention is illustrated, but in no way limited by the following Examples in which DSCG means disodium cromoglycate.

EXAMPLE 1

Male Charles River CD rats (150–250 g) receive 5 uCi $^{59}$Feferric citrate B.P. (radiochemical Centre) intravenously and are maintained on normal diet for at least one week. Two to three days before dosing the animals are housed singly in wire bottomed cages and put on a restricted diet of 15 g diet/day.

A blood sample is taken from a tail vein at this time. The animals are not fed on the morning of dosing. They are dosed twice at a 4–5 hour interval with anti-inflammatory agent (5 ml/kg in 0.1% 'Tween 80') as suspensions of the free acid. Where DSCG is administered it is given jointly with the anti-inflammatory drug. In some experiments an additional dose of DSCG alone is given 2 hours before the first joint dose. Sawdust trays under the cages are changed on the day of dosing and the faecal samples from each rat collected during the 4 days post-dose.

Radioactivity of blood and faeces is estimated in a $\gamma$-counter. Blood loss in the stools is calculated for each rat and results are expressed as the group mean ml/kg blood loss. Statistical treatment of the results is by a Mann-Whitney U-test. Indomethacin plasma levels were estimated spectrofluorimetrically by the method of Holt & Hawkins Brit. Med. J. 1, 1354 (1965).

The results are shown in Tables 1 and 2.

Table 1

| | The effect of DSCG upon aspirin-induced faecal blood loss | | | |
|---|---|---|---|---|
| Dose (mg/kg b.i.d.) | No of rats in group | ml/kg blood loss | $P_1$ | $P_2$ |
| (a) Control | 6 | 0.41 | | |
| Aspirin 300 | 7 | 0.55 | 0.07 | |
| | | | | 0.08 |
| Aspirin 300 + DSCG 100 | 7 | 0.48 | 0.13 | |
| (b) Control | 5 | 0.64 | | |
| Aspirin 300 | 5 | 1.80 | <0.01 | |
| Aspirin 300 + DSCG 100 | 5 | 1.73 | <0.01 | |
| Aspirin 300 + DSCG 100 + *DSCG 100 pre-dose | 5 | 0.91 | 0.03 | <0.01 |

*An additional dose of DSCG alone was administered 2 h before the first combined dose.

$P_1$ and $P_2$ are probability values derived from a Mann-Whitney U-test. The probability $P_1$ is associated with a difference between control and aspirin-treated groups. The $P_2$ value is associated with a difference between the aspirin and aspirin + DSCG groups.

Table 2

The effect of DSCG upon indomethacin-induced faecal blood loss

| Dose (mg/kg b.i.d.) | No. of rats in group | Faecal blood loss ml/kg increase after treatment | P |
|---|---|---|---|
| (a) Indomethacin 5 | 6 | 2.72 | |
| Indomethacin 5 + DSCG 100 | 7 | 0.75 | 0.03 |
| (b) Indomethacin 5 | 5 | 32.2 | |
| Indomethacin 5 + DSCG 100 | 6 | 14.8 | 0.06 |
| (c) Indomethacin 5 | 5 | 18.5 | |
| Indomethacin 5 + DSCG 100 | 5 | 4.0 | 0.02 |
| Indomethacin 5 + DSCG 50 | 5 | 3.7 | 0.02 |
| (d) Indomethacin 5 | 5 | 5.0 | |
| Indomethacin 5 + DSCG 50 | 4 | 1.07 | 0.14 |
| Indomethacin 5 + DSCG 20 | 5 | 2.45 | >0.2 |
| Indomethacin 5 + DSCG 10 | 5 | 1.86 | <0.2 |
| (e) Indomethacin 5 | 5 | 3.23 | |
| Indomethacin 5+ DSCG 20 | 5 | 1.01 | 0.08 |
| (f) Indomethacin 5 | 5 | 7.86 | |
| Indomethacin 5 + DSCG 100 | 5 | 4.63 | <0.2 |

*In expts 2c, d, e and f and additional dose of 100 mg DSCG alone was given 2 h before the first combined dose.
P value is the probability associated with a difference between the indomethacin and indomethacin + DSCG groups.

In some further experiments aspirin and DSCG were administered on a subacute basis. Animals were given one single dose of aspirin with or without DSCG by mouth each day for 5 consecutive days. Drugs were given one hour before feeding. Faeces were collected during the dosing period and for 3 days after administration of compound had ceased. The results of these experiments are shown in Table 3.

Table 3

The effect of DSCG upon faecal blood loss induced by subacute administration of aspirin

| Dose mg/kg daily | No of rats | ml/kg blood loss | $P_1$ | $P_2$ |
|---|---|---|---|---|
| (a) Aspirin 100 | 7 | 1.79 | | |
| Aspirin 100 + DSCG 100 | 7 | 1.16 | — | 0.08 |
| (b)* Control | 10 | 0.99 | | |
| Aspirin 100 | 9 | 1.97 | <0.001 | |
| Aspirin 100 + DSCG 25 | 10 | 1.74 | <0.001 | >0.1 |
| Aspirin 100 + DSCG 50 | 10 | 1.59 | <0.001 | >0.1 |
| Aspirin 100 + DSCG 100 | 10 | 1.29 | <0.05 | 0.05<p>0.1 |

* In this experiment DSCG was given as a suspension of the free acid.
$P_1$ and $P_2$ are probability values derived from a Mann-Whitney U test. The probability $P_1$ is associated with a difference between control and aspirin treated groups. The $P_2$ value is associated with a difference between the aspirin and aspirin + DSCG groups.

Example 2

| | mg/tablet |
|---|---|
| Aspirin | 300 |
| DSCG | 100 |
| Maize starch BP as binder | 15 |
| Maize starch as disintegrant | 45 |
| Microcrystalline cellulose BPC | 80 |
| Talc | 10 |
| | 550 |

Example 3

| | mg/tablet |
|---|---|
| Indomethacin | 25 |
| DSCG | 100 |
| Maize starch BP as binding | 7 |
| Maize starch as disintegrant | 25 |

Example 3-continued

| | mg/tablet |
|---|---|
| Lactose BP | 100 |
| Magnesium Stearate BP | 5 |
| | 262 |

Example 4

1. Central Core Formulation

Aspirin BP 300 mg
Maize Starch BP 45 mg

Sieve the aspirin through a 20 mesh sieve and the maize starch through a 40 mesh sieve. Mix these ingredients and compress into 'slugs'. Granulate the 'slugs' using a 12 mesh screen.

2. Formulation of Outer Layer

| | mg | % By weight |
|---|---|---|
| 1,3-Bis(2-carboxychromon-5-yloxy)-2-hydroxypropane, disodium salt | 100 | 49.8 |
| Sodium bicarbonate BP | 75 | 37.3 |
| Maize starch BP | 17.8 | 8.9 |
| Talc BP (sterilised) | 8.0 | 4.0 |
| Purified water BP | QS | QS |
| | 200.8 | 100.0 |

The sodium bicarbonate, after being passed through a 100 mesh screen, was mixed in a drum roller with the bis-chromone, which had been passed through a 60 mesh screen. Half the starch was then added, and the drum was rolled for about 20 minutes. The mixed powder was then transferred to a mixing bowl and damped down with the water (approximately 120 ml per kg of dry powder). The damped powder was then passed through an 8 mesh screen and was dried at 50° C for 2 hours, the dry product then being passed through a 16 mesh screen and blended with the talc and the remaining starch.

3. Intermediate Layer

An inert intermediate layer may, if desired, be used between the core and outer layer to delay the onset of disintegration and dissolution of the aspirin containing core. This intermediate layer may consist of fillers, e.g. lactose, dicalcium phosphate, a polymeric binder e.g. gelatin, polyvinylpyrrolidone, and a lubricant e.g. metallic stearates, talc etc. A suitable formulation comprises:

Lactose BP 120 mg
Dicalcium phosphate USP XVII 30 mg
Gelatin BP 3 mg
Magnesium stearate BP 1 mg The lactose and dicalcium phosphate, after being passed through a 40 mesh sieve, were mixed in a planetary mixer for 10 minutes and damped down with a 12% w/w aqueous solution of the gelatin (approx 150 ml solution per kg of dry powder). The damped down mixture was then passed through an 8 mesh screen and dried at 60° C for 2 hours, the dry product then being passed through a 20 mesh screen and blended with the magnesium stearate.

Compression

The core formulation may be compressed into a solid core and the intermediate and outer layers may be compressed around this core using a suitable rotary compression coating machine, e.g. a 'Manesty,' 'Drycota' or 'Bicota' machine.

We claim:

1. A pharmaceutical composition comprising 1,3-bis-(2-carboxy-chromon-5-yloxy)propan-2-ol, or a pharmaceutically acceptable salt thereof, as active ingredient, in combination with about 0.12 to 6000 parts by weight of aspirin or about 0.02 to 1000 parts by weight of indomethacin to each part by weight of active ingredient.

2. A composition according to claim 1 comprising from 1.2 to 600 parts by weight of aspirin to each part by weight of active ingredient.

3. A composition according to claim 1 comprising from 0.3 to 100 parts by weight of indomethacin to each part by weight of active ingredient.

4. A composition according to claim 1 comprising from 100 to 600 mg of aspirin and from 0.1 to 500 mg of active ingredient in unit dosage form.

5. A composition according to claim 1 comprising from 10 to 100 mg of idomethacin and from 0.1 to 500 mg of active ingredient in unit dosage form.

6. A composition according to claim 1 comprising from 1 to 200 mg of active ingredient in unit dosage form.

7. A composition according to claim 1 containing up to 100 mg of active ingredient in unit dosage form.

8. A composition according to claim 1 in a form adapted to be administered oesophageally.

9. A composition according to claim 1 wherein the composition, or one or more of the components thereof, is formulated in sustained release form.

10. A composition according to claim 1 adapted to release some or all of the active ingredient first and to release the aspirin or indomethacin later.

11. A pharmaceutical package comprising at least one unit dose of 1,3-bis-(2-carboxychromon-5-yloxy)propan-2-ol, or a pharmaceutically acceptable salt thereof, as active ingredient, and at least one unit dose of indomethacin or aspirin.

12. A package according to claim 11, wherein the unit doses are arranged in an order which facilitates the administration to a mammal of a unit dose of active ingredient prior to or simultaneously with a unit dose of aspirin or indomethacin.

13. A method of administering aspirin or indomethacin to a mammal with inhibition of adverse gastrointestinal effects due to said aspirin or indomethacin which method comprises orally administering to said mammal a composition according to claim 1.

14. A method of inhibiting adverse gastrointestinal effects created in a mammal by administration of aspirin or indomethacin, which method comprises administering to said mammal an effective amount of 1,3-bis-(2-carboxy-chromon-5-yloxy)propan-2-ol or a pharmaceutically acceptable salt thereof, sequentially or substantially simultaneously with the administration of said aspirin or indomethacin.

* * * * *